United States Patent [19]
Riihimaki et al.

[11] Patent Number: 4,854,475
[45] Date of Patent: Aug. 8, 1989

[54] INSTRUMENT CASSETTE

[75] Inventors: Karl Foll, Glenview, Ill.; Roy Riihimaki; Richard D'Amico, both of Libertyville, Ill.

[73] Assignee: Hu-Friedy Manufacturing Co., Inc., Chicago, Ill.

[21] Appl. No.: 158,384

[22] Filed: Feb. 22, 1988

Related U.S. Application Data

[63] Continuation-in-part of Ser. No. 757,789, Jul. 22, 1985, abandoned.

[51] Int. Cl.⁴ .............................................. B65D 43/14
[52] U.S. Cl. .................................... 220/337; 220/340; 220/342; 220/22.1; 206/369
[58] Field of Search ............... 220/342, 340, 337, 339, 220/334, 22, 22.1, 22.3, 22.5, 326; 206/369, 370, 438, 439, 594; 422/300

[56] References Cited

U.S. PATENT DOCUMENTS

| | | | |
|---|---|---|---|
| 2,117,228 | 5/1938 | Stuchbery | 220/340 |
| 3,572,536 | 3/1971 | Wehner | 220/22.1 |
| 4,099,648 | 7/1978 | Kirkton | 220/340 |
| 4,199,072 | 4/1980 | Jacks | 220/340 |

Primary Examiner—Willis Little
Attorney, Agent, or Firm—Laff, Whitesel, Conte & Saret

[57] ABSTRACT

A cassette for sterilization and storage of instruments, incorporating improved instrument-locating and retaining means and improved hinge and latch mechanisms. The cassette is fabricated of metallic materials having superior heat resistance, and is designed to be stored in stacked relationship with other such cassettes.

16 Claims, 3 Drawing Sheets

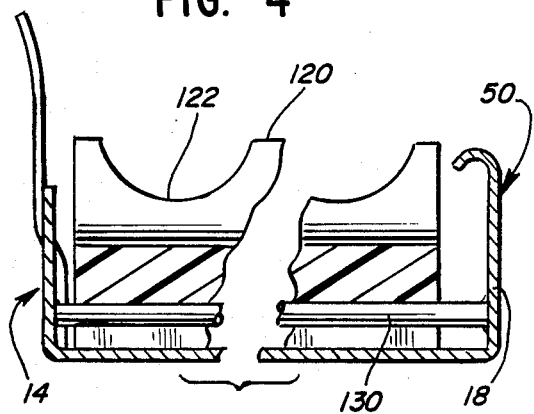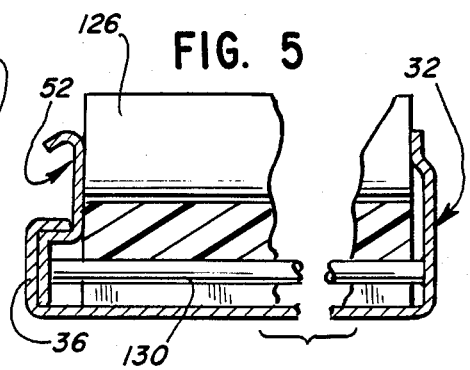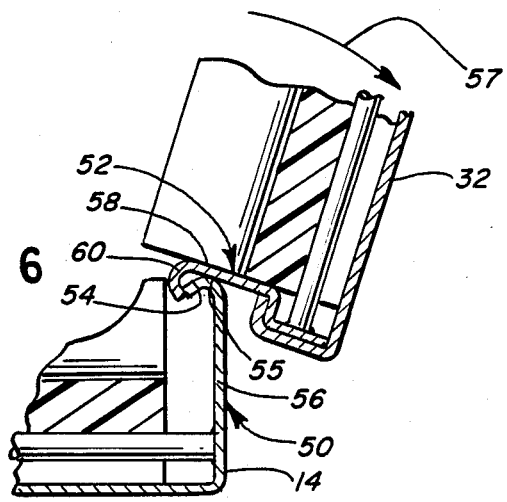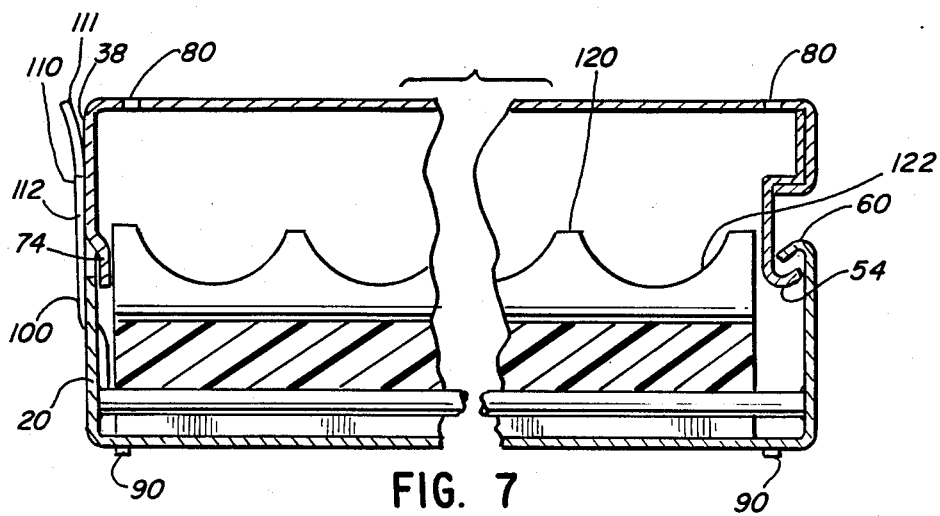

INSTRUMENT CASSETTE

This application is a continuation-in-part of co-pending application Ser. No. 757,789, filed July 22, 1985, which has one inventor in common with this application, and is assigned to the same assignee, now abandoned.

BACKGROUND OF THE INVENTION

This invention relates to medical/dental instrument cassettes, particularly for the purpose of sterilizing such instruments.

In the past, instruments were sterilized while loose, and subsequently selected for use from a loose array of instruments. Subsequently, dental instruments were sterilized while loose, and then organized in trays in the sequence in which they were to be used. Most recently, dental instruments have been organized in the trays first, and then sterilized and used. However, the trays originally used for this purpose were reinforced wire mesh baskets which were costly, unstackable, and had hinged lids which were difficult to keep open, and were subject to discoloration, breakage, and debris entrapment. Plastic cassettes with superior facilities for organizing instruments have also been used, but some of the plastic materials adopted for this purpose do not seem able to withstand sterilization heat over the lifetime of the cassette without crazing, flaking, and otherwise deteriorating. These cassettes were also stackable one atop the other for easier storage.

SUMMARY OF THE INVENTION

The invention provides a cassette for sterilization and storage of instruments which incorporates improved means for retaining the instruments in place within the cassette so as to keep them in a predetermined stable arrangement. The cassette is stackable with other cassettes or like design, but can also stand independently in a variety of stable attitudes. In addition, it features improved hinge and latch mechanisms, and heat-resistant materials which will not deteriorate when subjected to many sterilization cycles.

These and other aspects, objects and advantages of the invention are explained in a detailed description of the preferred embodiment of the invention, which accompanies the following drawing in which

BRIEF DESCRIPTION OF THE DRAWINGS

FIG. 4 is a transverse cross-sectional view of the lower tray of the cassette;

FIG. 5 is a similar cross-sectional view of the upper cover of the cassette;

FIG. 6 is a fragmentary transverse cross-sectional view of the releasable hinge mechanism joining the tray and cover together, seen in the initial stage of disengagement;

FIG. 7 is a transverse cross-sectional view of the cassette 10 in its closed condition;

DETAILED DESCRIPTION OF THE PREFERRED EMBODIMENT

The medical or dental instrument cassette 10 of this invention is preferably made of a metallic material so that it can withstand repeated cycling through a process of autoclave sterilization with a plurality of medical or dental instruments kept in fixed arrangements in the cassette. A plurality of such cassettes 10 are adapted to be stacked one atop the other for ease of storage.

Figure 3:
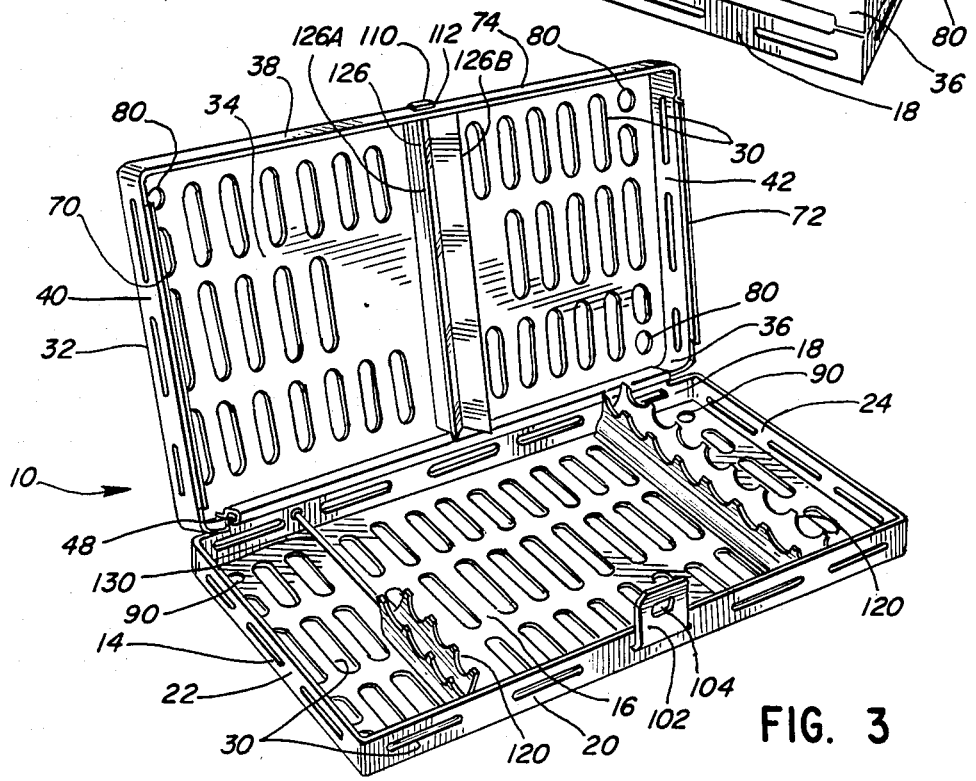
FIG. 3 is a front perspective view of the cassette seen in the open condition.

Referring to FIG. 3, it will be seen that the cassette comprises a lower rectangular tray 14 and an upper rectangular cover 32. The lower tray comprises a bottom wall 16 and four upstanding sidewalls 18, 20, 22, 24 defining a tray interior. The bottom wall and tray sidewalls are formed of a sterilization-heat-resistant material, preferably a rust-resistant metal, and are perforated by a plurality of openings 30 to allow free passage of sterilization steam through the cassette.

The upper cover 32 has a top wall 34 and four depending sidewalls 36, 38, 40, 42 defining a cover interior. The top wall and cover sidewalls are also formed of a sterilization-heat-resistant material, preferably a rust-resistant metal, and are also perforated by a plurality of openings 30 for the purpose described above.

A hinge mechanism 48 located on the top of the rear tray sidewall 18 and the bottom of the rear cover sidewall 36 releasably joins the cover 32 to the tray 14. As a result, the cover 32 is rotatable relative to the tray 14 about the hinge mechanism 48 to and from open and closed positions.

The hinge mechanism 48 also permits the cover 32 and tray 14 to be separable from each other when the cover rotates past the perpendicular position relative to the tray. For this purpose, hinge mechanism 48 comprises a pair of cooperating J-shaped hinge members 50 and 52. A tray hinge member 50 is integrated with the rear tray sidewall 18 of tray 14 and projects upwardly therefrom (see FIG. 4), and a cover hinge member 52 is connected (as by brazing, welding, or the like) to the rear sidewall 36 of cover 32 (see FIG. 5), and projects downwardly therefrom to engage the tray hinge member 50 when the cover is closed. The entire hinge mechanism 48, including tray hinge member 50 and cover hinge member 52, is formed of a sterilization-heat-resistant material, preferably a rust-resistant metal.

Referring to FIG. 6, tray hinge member 50 includes a straight upstanding portion 56 and a curved hook portion 54. Cover hinge member 52 similarly includes a straight portion 58 and a curved hook portion 60. Hinge mechanism 48 is operative when the curved hook portion 54 of tray hinge member 50 engages and rotates about the curved hook portion 60 of cover hinge member 52 to permit the cover 32 to assume the closed and opened positions.

FIG. 7 illustrates the two hook portions 54 and 60 interengaging to secure the cover and tray together along their rear sidewalls when the cover is in the closed position. FIG. 6 illustrates the cover at the point where it has rotated at least about 100 degrees toward the open position. At that point the hook portion 60 has rotated from below hook portion 54 to the top of hook portion 54, permitting the cover 14 simply to be lifted off the tray 14.

But in addition, a self-disengagement feature comes into operation when the angle between the tray 14 and the cover 32 reaches approximately 100°-110°, the exact position being determined by the degree of curvature of curved hook portions 54 and 60. These portions are hookingly inter-engaged, in the manner seen in FIG. 7, from the fully closed position of FIG. 7 and through at least about 100 degrees of opening rotation, up to the point seen in FIG. 6 at which disengagement begins. Then further opening rotation of the cover 32 causes the straight portion 58 of cover hinge member 52 to contact a peak 55 of the curved portion 54 of tray hinge member 50, after which continued rotation of the cover 32 (as indicated by arrow 57) will cause cover hinge member 52 to pivot about peak 55, releasing the hook portion 60 from inter-engagement with the hook portion 54, and thereby resulting in complete separation of the cover 32 from tray 14. This self-disengagement feature facilitates easy and rapid separation of the cover 32 from the tray 14 upon opening.

Cover 32 is re-attached to tray 14 by placing the J-shaped cover hinge member 52 over the curved portion 54 of tray hinge member 50 and rotating the cover 32 in the direction opposite to arrow 57 until the hook portions 54 and 60 are re-engaged, and thereafter continuing to rotate the cover until the cassette is completely closed.

Figure 8:
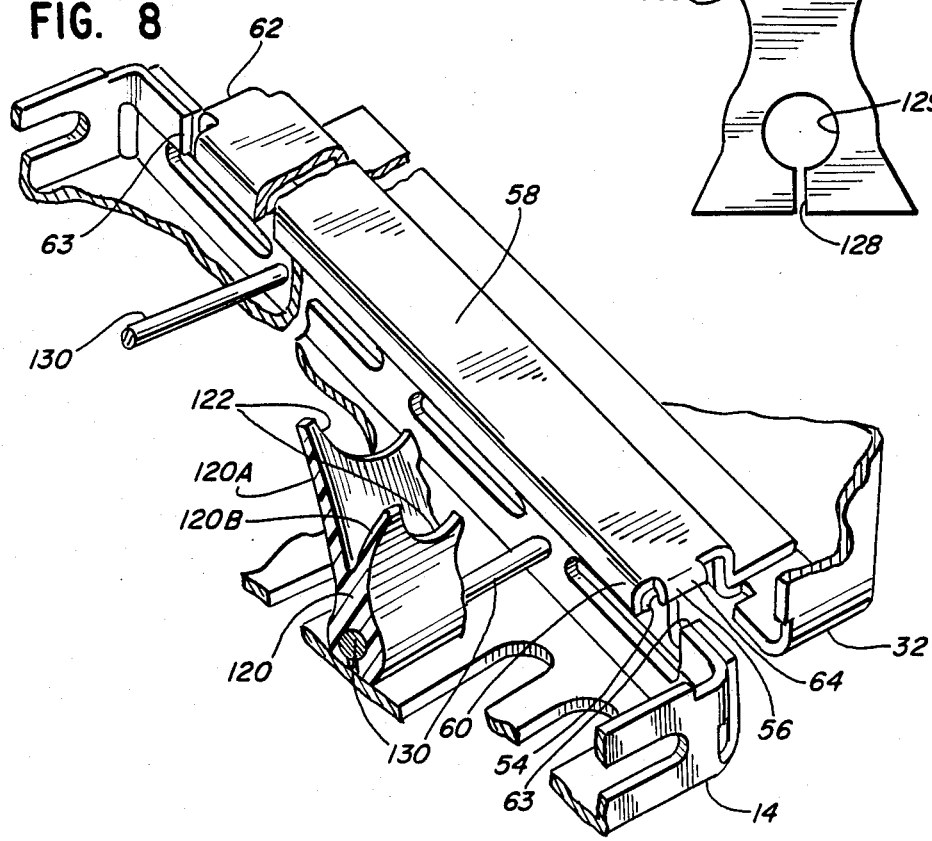
FIG. 8 is a fragmentary perspective view of the hinge mechanism and adjacent structures, seen when the cover is completely open.

As seen in FIG. 8, cover hinge member 52 is aligned relative to the tray hinge member 50 by means of curved locating tabs 62 and 64 curving from the opposite extremities of the straight portion 58 of cover hinge member 52, and embracing the respective extremities of hook portion 54 to prevent lateral motion of the cover 14 relative to the tray 32. Notches 63 are formed at two locations in the rear sidewall 18 of the tray to accommodate these locating tabs 62 and 64.

When the cassette 10 is in the closed position, lateral movement of the cover 32 relative to the tray 14 is further prevented by flanges 70, 72 (FIG. 3) extending from cover sidewalls 40 and 42 respectively, and contacting the insides of tray sidewalls 22, 24.

Similarly, forward and rearward movement of the closed cover 32 relative to tray 14 is restricted by hinge mechanism 48 and by a lip 74 (FIGS. 3 and 7) curving inwardly and extending downwardly from the front cover sidewall 20 to contact the inside of the tray front sidewall 20.

Figure 2:
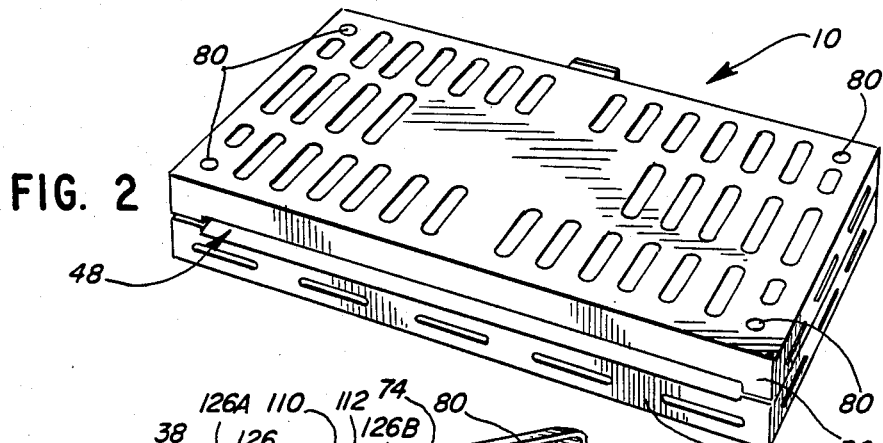
FIG. 2 is a rear perspective view of the cassette, also seen in the closed condition.

As best shown in FIG. 2, tray hinge member 50 and cover hinge member 52 of hinge mechanism 48 are recessed inwardly of the plane defined by the rear tray sidewall 18 and the rear cover sidewall 36 when the cover 32 is in the closed position. Because of this recess the rear sidewall plane provides a planar back surface for stable upright placement of the cassette 10. The sidewalls 22, 40 and 24, 42 also provide similar planar side surfaces for stable, upright placement of the cassette.

Referring to FIGS. 2 and 7, stacking feet 90 of a spherical or like shape extend downwardly from the tray bottom 16. Receptor depressions 80 in the cover top 34 are formed to receive the stacking feet 90 so that when a number of cassettes 10 are stacked, the feet 90 of the cassette above will fit within the receptors 80 of the cassette below. The resulting interfit creates a locking action which prevents sliding of one cassette relative to another. The locking action permits detachable unification of contiguous cassettes into stacks that are capable of fitting into a variety of available storage or sterilization spaces. The stacking feet 90 and receptors 80 also allow for stacking of a cassette tray 14 on top of its own cover 32.

Figure 1:
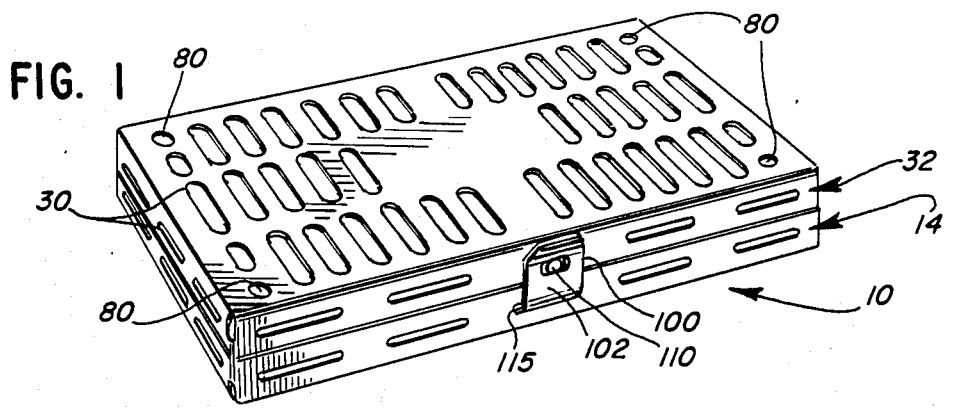
FIG. 1 is a front perspective view of the cassette of this invention, seen in a closed condition.

Referring to FIGS. 1, 3 and 7, a latch 100 is provided for locking the cassette in the closed position. This latch includes an upstanding arm 102 and a detent stud 110. The lower portion of the latch arm 102 is connected, as by brazing, welding or the like, to the inside of the front tray sidewall 20. The upper part of the latch arm 102 passes through a slot 115 formed in the front tray sidewall 20 and extends upwardly to form an essentially vertical spring arm (FIGS. 3, 7). The latch stud 110 is struck forwardly from the front cover sidewall 38 and is formed with a downwardly sloping ramp portion 112 (FIGS. 3, 7). A detent opening 104 formed in latch arm 102 (FIG. 3) receives the latch stud 110 when the cassette is in the latched position.

During assembly of the cassette 10, latch arm 102 is bent slightly in a direction toward the rear of the cassette. When the cassette is in the closed or latched position, the prebending of latch arm 102 biases it toward the latch stud 110 and against the front cover sidewall 38, causing the stud to enter the detent opening 104 to achieve secure closure of the cassette.

The latch mechanism closes automatically upon closing of the cover 32, as best described with reference to FIG. 7. Upon rotation of the tray cover 32 toward the tray 14, just before the cover reaches the closed position, ramp portion 112 of latch stud 110 cammingly engages an outwardly sloping portion 111 at the upper extremity of latch arm 102. Further rotation of cover 32 causes latch arm 102 to flex outwardly in order to move past the ramp portion 112 of latch stud 110. Finally, when the cover reaches the closed position, latch stud 110 enters the detent opening 104 in latch arm 102. At that point the latch arm 102, due to its rearward spring bias, snaps over latch stud 100 and comes to rest firmly against front cover sidewall 38 with the stud 100 received within the opening 104. Subsequently the latch holds the cassette firmly closed, and cannot be released without a deliberate effort to flex the latch arm forwardly and thus release the stud 100 from the opening 104.

The latch parts are all formed of a sterilization-heat-resistant material, preferably a rust-resistant metal.

In the interior of the cassette are instrument-retaining and locating members 120 and an instrument clamping member 126, as shown in FIG. 3. The locating members 120 are formed of a flexible, compressible, sterilization-heat-resistant material such as silicone rubber, and are installed in the bottom tray. They each have a pair of wings 120A and B (FIG. 9) which have scalloped upper edges to define a plurality of recesses 122 (FIG. 10) for resiliently nesting medical or dental instruments of various shapes. The clamping member 126 is formed of a similar flexible, compressible sterilization-heat-resistant material, and is installed in the upper cover. It is formed with a pair of straight-edged wings 126A and B (FIG. 3) which, when the cassette cover is closed, function to exert resilient pressure against the instruments received within the nesting recesses 122 of the locating members 120, and thus prevent them from being dislodged.

Both the locating members 120 and the clamping member 126 are detachably secured to the cassette by means of cylindrical mounting rods 130. Rods 130 are preferably made of a sterilization-heat-resistant material, such as a rust-resistant metal, and are rigidly connected to the tray sidewalls 18, 20 and the cover sidewalls 36, 38, as by brazing, welding, or the like.

Figure 9:
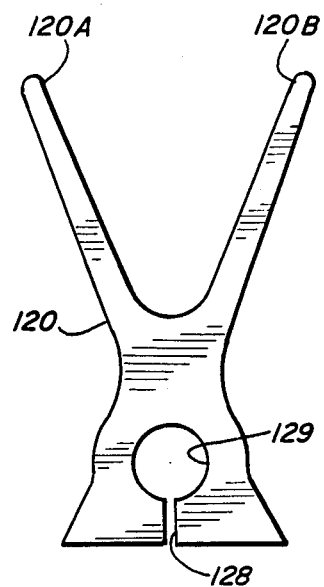
FIG. 9 is an end elevational view of an instrument locating and retaining member installed in the cassette.
Figure 10:
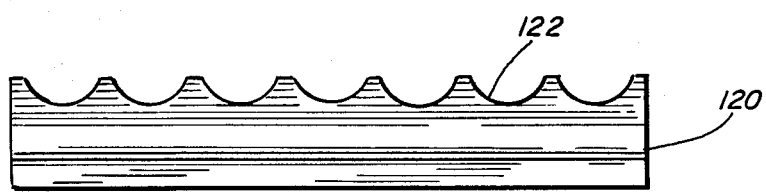
FIG. 10 is a side elevational view of the same instrument locating and retaining member.

The flexible members 120 and 126 are each formed with an axially elongated slot 128 leading to an axially elongated mounting cavity 129 of circular cross-section extending for the entire lengths of members 120 and 126 (see, for example, FIG. 9). These cavities allow the members 120 and 126 to be attached to and detached from rods 130. FIG. 8 shows one of the members 120 mounted upon one of the rods 130, with the rod received within the cavity 129. This feature allows for easy installation and replacement of the members 120 and 126.

As seen in FIG. 7, when an empty cassette 10 is in the closed position, the curved hook portions 54, 60 of hinge mechanism 48 are separated by a distance S. This separation distance is closed up when instruments are placed in the nesting hollows 122, and thus allows the cassette to accommodate its contents. For larger-sized instruments additional expansion room is provided by compressing the members resilient 120 and 126.

It will now be appreciated that the present invention provides a convenient stackable cassette for sterilization and storage of instruments, which features improved hinge and latch mechanisms, improved means for retaining the instruments in place within the cassette, and heat-resistant materials.

Those who are skilled in the art will readily perceive how to modify the invention. Therefore, the appended claims are to be construed to cover all equivalent structures which fall within the scope and spirit of the invention.

The invention claimed is:

1. A cassette comprising:
a lower tray member and an upper cover member cooperating to form an enclosure;
a hinge mchanism for hinging said tray and cover members together for opening and closing rotative motion of said cover member relative to said tray member;
said hinge means including first J-shaped hinge means on at least one of said members and second hinge means on the other of said members arranged to be encircled by said first hinge means to prevent separation of said cover member from said tray member over a range of rotative cover member positions from fully closed to partially open relative to said tray; and to permit separation of said cover member from said tray member upon continued rotation of said cover member past said partially open position.

2. A cassette as in claim 1 wherein said first hinge means is associated with said upper cover member, said second hinge means is associated with said lower tray member, said first hinge means is hooked under said second hinge means when said cover is closed, and is arranged to rotate to the top of said second hinge means at a predetermined degree of opening of said cover member defining said partially open position, said first hinge means being upwardly releasable from said second hinge means for ready separation of said cover member by lifting said cover member upwardly from said tray member at said predetermined cover member position.

3. Apparatus as in claim 2 further comprising means on said tray and cover members arranged to abut each other at said predetermined cover member position, in such manner that further rotation of said cover member in the opening direction causes said cover member to rotate about said point of abutment on said tray member in a manner to lift said first hinge means upwardly free of said second hinge means to automatically separate said cover member from said tray member.

4. Apparatus as in claim 3 wherein said second hinge means is also J-shaped and said first and second hinge means are arranged for mutually hooking engagement over a range of cover member positions from fully closed to partially open.

5. Apparatus as in claim 4 wherein said hinge mechanism is formed of a metallic material.

6. Apparatus as in claim 4 wherein said cassette and said hinge mechanism are formed of a metallic material.

7. Apparatus as in claim 1 further comprising means projecting from one of said cassette members into the other of said cassette members and interfitting therewith in a manner to prevent misalignment between said cassettes members.

8. Apparatus as in claim 1 further comprising spring-loaded latch means for releasably securing said cassette members to each other.

9. Apparatus as in claim 8 wherein said latch means is made of a metallic material.

10. Apparatus as in claim 9 wherein said cassette members are made of a metallic material.

11. Apparatus as in claim 8 wherein said latch means is self-closing.

12. An instrument cassette comprising: at least one elongated instrument retaining member having a first portion adapted to support said instruments; a second portion of said retaining member being formed with mounting cavity means; and elongated supporting means mounted within said cassette, said retaining member being mounted over said supporting means with said supporting means received within said mounting cavity means.

13. Apparatus as in claim 12 wherein said mounting cavity means is re-entrant and comprises entrance and exit means connecting to the exterior of said retaining member, said retaining member being formed of a sufficiently flexible material to permit said supporting means to enter into and be withdrawn from said mounting cavity means through said entrance and exit means, whereby said retaining member is removably and replaceably mounted on said supporting means.

14. Apparatus as in claim 12 wherein said supporting means is a substantially cylindrical rod mounted within said cassette, and said mounting cavity means is a substantially cylindrical cavity.

15. Apparatus as in claim 14 wherein said rod is made of a metallic material.

16. Apparatus as in claim 15 wherein said cassette is made of a metallic material.

* * * * *

UNITED STATES PATENT AND TRADEMARK OFFICE
CERTIFICATE OF CORRECTION

PATENT NO. : 4,854,475

DATED : August 8, 1989

INVENTOR(S) : Karl Zoll, Roy Riihimaki, Richard D'Amico

It is certified that error appears in the above-identified patent and that said Letters Patent is hereby corrected as shown below:

On the title page, item [75]:
  Inventor listed as Karl Foll should be Karl Zoll.

Column 1, line 39, the word "or" should be --of--.

Column 5, line 38, the word "mchanism" should be --mechanism--.

Signed and Sealed this

Twenty-fifth Day of December, 1990

Attest:

HARRY F. MANBECK, JR.

*Attesting Officer*          *Commissioner of Patents and Trademarks*